United States Patent [19]
Young et al.

[11] Patent Number: 5,217,012
[45] Date of Patent: Jun. 8, 1993

[54] NONINVASIVE OXIMETER PROBE

[75] Inventors: Robert L. Young, Waukesha, Wis.;
Bert D. Heinzelman, Tenafly, N.J.;
David A. Lovejoy, Waukesha, Wis.

[73] Assignee: Sensor Devices Inc., Waukesha, Wis.

[21] Appl. No.: 748,700

[22] Filed: Aug. 22, 1991

[51] Int. Cl.⁵ .................................................. A61B 5/00
[52] U.S. Cl. ........................................ 128/633; 356/41
[58] Field of Search .................. 128/633, 664, 665; 356/39, 41

[56]  References Cited
U.S. PATENT DOCUMENTS

| 3,599,629 | 8/1971 | Gordy. |
| 3,769,974 | 11/1973 | Smart et al.. |
| 4,091,803 | 5/1978 | Pinder. |
| 4,350,165 | 9/1982 | Striese. |
| 4,830,014 | 5/1989 | Goodman et al.. |
| 4,867,165 | 9/1989 | Noller et al. ........................... 128/633 |
| 4,928,691 | 5/1990 | Nicolson et al. ..................... 128/633 |
| 5,054,488 | 10/1991 | Muz ....................................... 128/633 |
| 5,058,588 | 10/1991 | Kaestle ................................. 128/633 |

Primary Examiner—William E. Kamm
Assistant Examiner—Kevin Pontius
Attorney, Agent, or Firm—Foley & Lardner

[57] ABSTRACT

An improved noninvasive, electrooptical sensor probe is suitable for removable adhesive attachment to the skin of a patient to measure light extinction during transillumination of the blood-perfused tissue beneath the skin. The probe has a flexible generally U-shaped, web-like support structure having spaced, opposed upper and lower inner surfaces. A light source such as an LED is mounted in the support structure and positioned to emit light from one of the inner surfaces. A photosensor is also mounted in the support structure and positioned on the other of the inner surfaces to detect light emitted by the light source. A U-shaped alignment member is disposed in the support structure and extends substantially from the light source to the photosensor to hold the probe into the desired shape for use and aid in aligning the LED and photosensor.

8 Claims, 3 Drawing Sheets

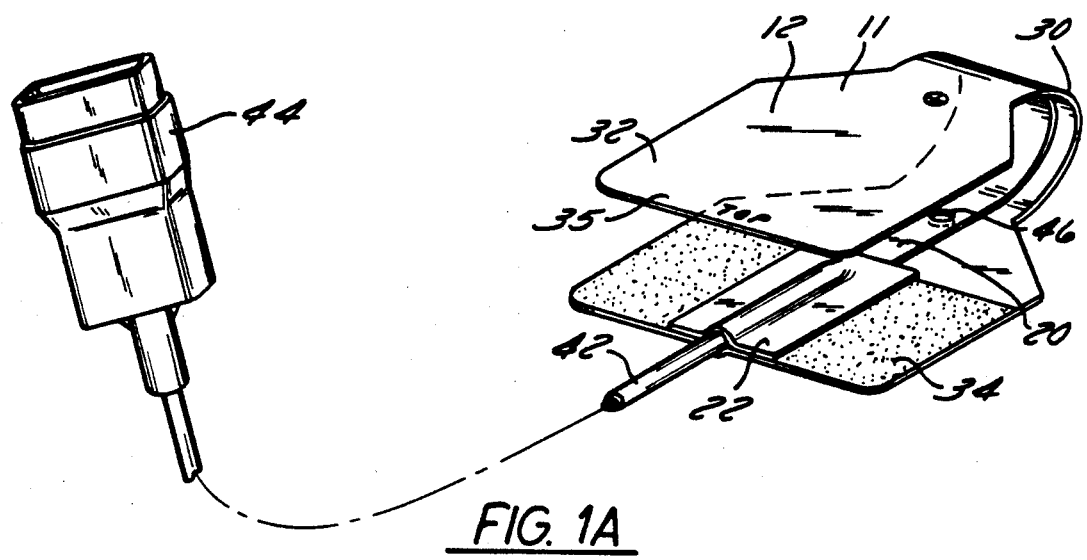
FIG. 1A
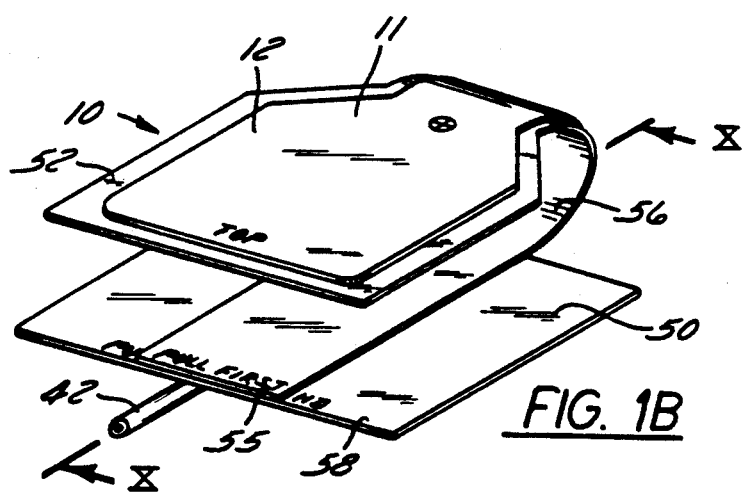
FIG. 1B
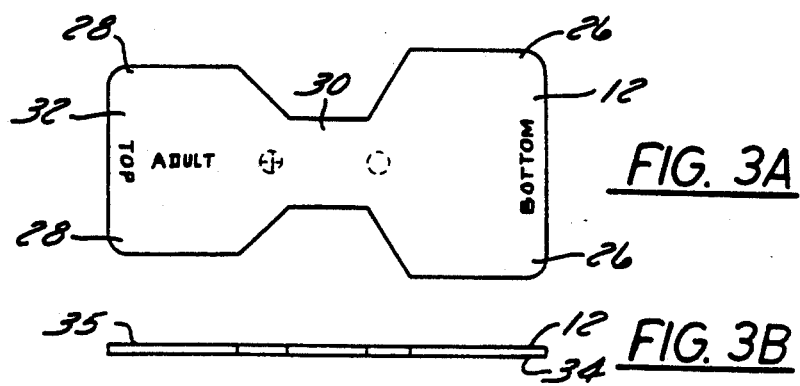
FIG. 3A
FIG. 3B

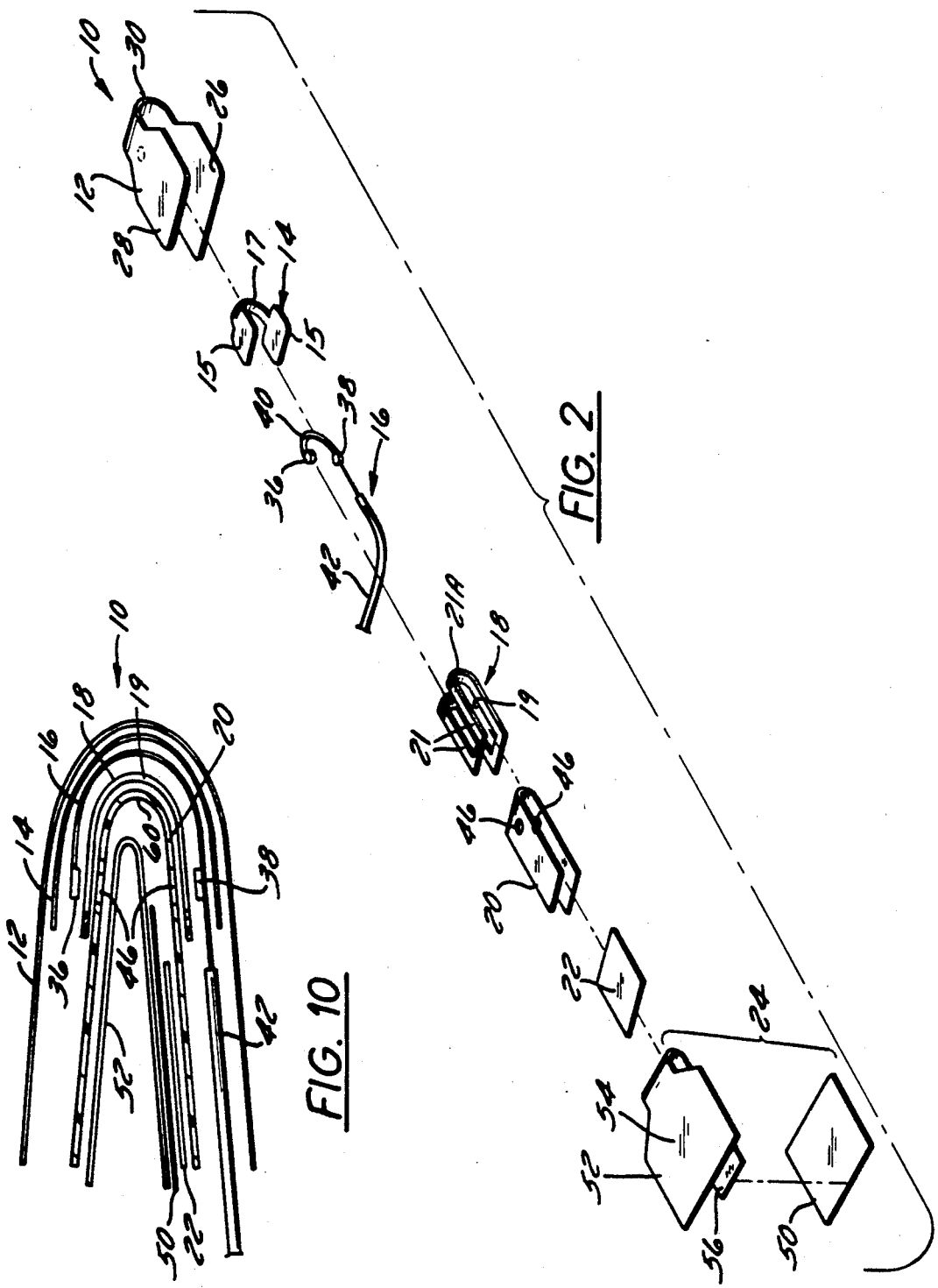

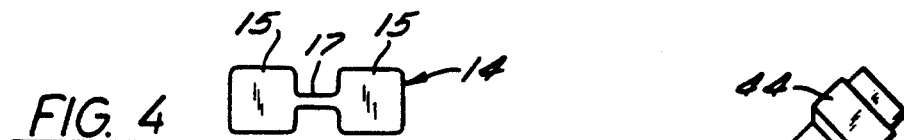
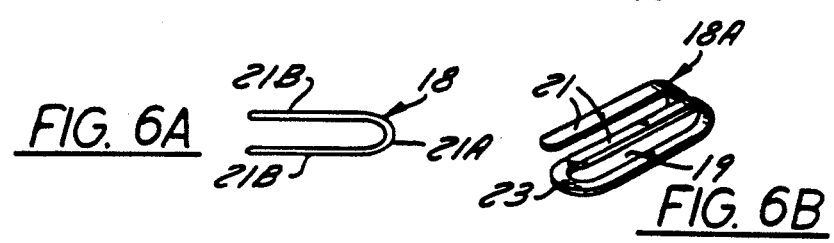
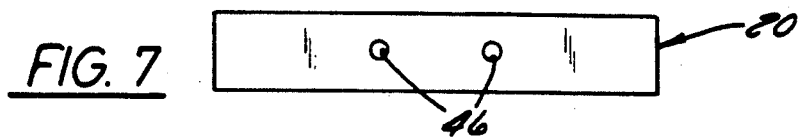
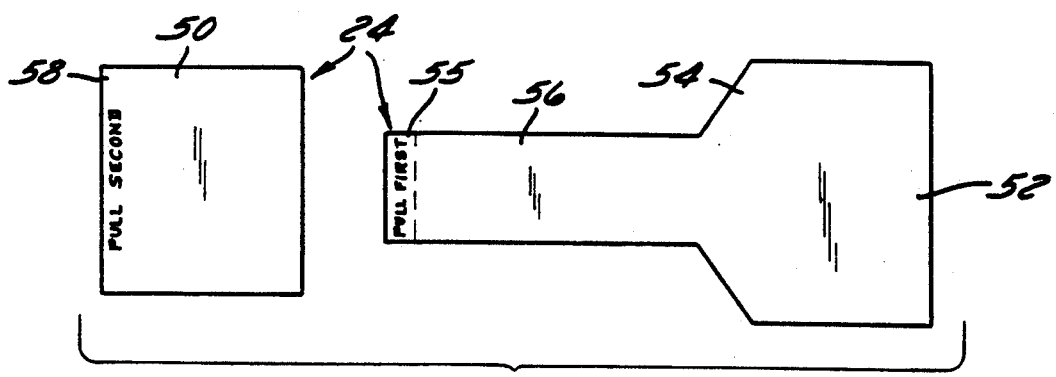

NONINVASIVE OXIMETER PROBE

TECHNICAL FIELD

This invention relates generally to pulse oximetry, particularly to oximeter probes of the type which transmit light through blood-perfused tissue.

BACKGROUND OF THE INVENTION

Pulse oximetry involves the continuous, noninvasive monitoring of the oxygen saturation level in blood perfused tissue to provide an early indication of impending shock. An oximeter probe (sensor) is secured to the patient and provides an electrical signal to an oximeter "box." The box houses electronic circuitry to process this electrical signal and generate human-readable indicia of the patient's blood oxygen saturation level. Both disposable and non-disposable sensor probes for this purpose are widely used.

Current disposable probes typically comprise a flexible substrate (e.g., foam, fabric) having a light emitting diode (LED) and a photosensor spaced apart from one another and secured to the substrate. The substrate is adhesively attached to a patient's skin, preferably on the finger, nose, or ear of an adult, or on the foot of an infant. When the sensor is secured to the patient, the tissue is disposed between the LED and the photosensor such that light emitted by the LED passes through the tissue and is received by the photosensor.

Changes in the amount of light absorbed by the photosensor are caused by changes in the optical absorption of certain wavelengths by the blood-perfused tissue. The absorption characteristics of the transilluminated tissue are related to the oxygen saturation level of hemoglobin flowing through the tissue. These variations in light absorption caused by changes in oxygen saturation permit the direct, noninvasive monitoring of arterial oxygen content.

These and other similar medical devices are well known. See, for example, Smart et al. U.S. Pat. No. 3,769,974, which relates to a photo-optical blood pulse measurement transducer, and Pinder U.S. Pat. No. 4,091,823, which relates to a transducer for monitoring heart rate.

A variety of support structures have been devised for adhering probes and electrodes to skin surfaces. See, for example, Striese U.S. Pat. No. 4,350,165, and Gordy U.S. Pat. No. 3,599,629, which discloses a disposable biopotential skin electrode comprising a deformable, synthetic polymeric material having an adhesive coating.

Goodman et al. U.S. Pat. No. 4,830,014 describes a sensor for measuring arterial oxygen saturation using noninvasive photoelectric techniques. In a preferred embodiment, the sensor comprises a flexible, planar substrate having an LED mounted near a first end thereof and a photosensor spaced apart from the LED and mounted in a second end thereof. The sensor further includes an adhesive backing to facilitate close conformance to a patient's fingertip, such that the blood-perfused tissue lying between the LED and the photosensor is transilluminated by the light from the LED. Beginning at column 1, line 44, Goodman states that a common problem with existing oximeter sensors arises from their incompatibility with a patient's anatomy. More particularly, the physical construction of the sensors renders them bulky and difficult to securely fasten to a patient's appendage (e.g., finger, foot, nose, ear), resulting in differential motion between the patient and the sensor during patient movement. This relative motion, in turn, causes signal distortion (motion artifact.)

Prior art attempts to eliminate motion artifact often produced undesirable occluding effects due to, for example, the spring pressure applied by clip-like devices, resulting in insufficient pulse amplitude to reliably measure blood flow. Goodman proposed solving this problem by integrating the light source and photosensor into the adhesive fastener. The present invention improves further upon the Goodman probe by substantially changing the way in which the probe is mounted to an extremity and the way it maintains alignment between the LED and photosensor.

SUMMARY OF THE INVENTION

A noninvasive, electrooptical sensor probe according to the invention is suitable for removable adhesive attachment to the skin of a patient to measure light extinction during transillumination of the blood-perfused tissue beneath the skin. Such a probe includes a flexible, initially (and subsequently) substantially U-shaped, web-like support structure having spaced, opposed upper and lower inner surfaces, a light source mounted in the support structure and positioned to emit light from one of the inner surfaces, a photosensor mounted in the support structure and positioned on the other of the inner surfaces to detect light emitted by the light source, adhesive tapes or other suitable means for removably securing the support structure to the skin, particularly to a concave skin surface such as a fingertip, and a generally U-shaped alignment member disposed in the support structure and extending substantially from the light source to the photosensor. The convexity of the skin portion inserted between the light source and the photosensor allow the respective light-emitting and light-responsive surfaces of each to be inclined toward one another so that light from the light source transilluminates the tissue between the light source and the photosensor. The light-responsive surface of the photosensor thereby detects at least a part of the light from the light source. The light reading is transmitted to an oximeter box in a manner well known in the art to determine the oxygen saturation level in the perfused tissue.

BRIEF DESCRIPTION OF THE DRAWINGS

The probe of the invention is described below in conjunction with the appended drawings, wherein like designations denote like elements, and:

FIG. 1A is a perspective view of a sensor probe according to the invention for adult use with release tapes removed to show a slide which facilitates insertion of the patient's finger into the probe;

FIG. 1B is the same view as FIG. 1A, showing release tapes adhered to the inner surface of the probe;

FIG. 2 is an exploded view of the probe shown in FIG. 1B;

FIGS. 3A and 3B are plan and side views, respectively, of the outer tape shown in FIGS. 1A, 1B and 2;

FIG. 4 is a plan view of the light block tape shown in FIG. 2;

FIG. 5 is a plan view of the sensor assembly shown in FIG. 2;

FIG. 6A is a side view of the alignment member shown in FIG. 2;

FIG. 6B is a perspective view of an alternative embodiment of an alignment member of the invention;

FIG. 7 is a plan view of the inner tape shown in FIG. 2;

FIG. 8 is a plan view of the positioning slide shown in FIG. 2;

FIG. 9 is a plan view of the release tape assembly shown in FIGS. 1B and 2; and

FIG. 10 is an exploded, cross-sectional view taken along line X—X in FIG. 1B.

DETAILED DESCRIPTION OF PREFERRED EMBODIMENTS

With reference to FIGS. 1A, 1B, 2 and 10, a generally U-shaped probe 10 according to the invention includes a web-like support structure 11 (including an outer tape 12, a light block tape 14, and other components as described below), an electrical sensor assembly 16, an alignment member 18, an inner tape 20, a positioning slide 22, and a release tape assembly 24. During manufacture, the foregoing components are sequentially assembled, such as shown in FIG. 2, into the U-shaped sensor shown in FIG. 1B.

Referring to FIGS. 3A and 3B, outer tape 12 has a pair of laterally extending, generally rectangular bottom wings 26 at one end thereof, a similar, slightly shorter pair of lateral top wings 28 at the other end thereof, and a narrow bridging portion (bight) 30 therebetween. The words "Top", "Bottom", and "Adult" and other suitable symbols may be printed on an outer surface 32 of tape 12 to aid in the identification of the probe and to facilitate application to a patient. Tape 12 has an inner surface including a lower inner surface 34 and an upper inner surface 35 which are spaced from each other. Inner surfaces 34, 35 of outer tape 12 are coated with a pressure sensitive adhesive at wings 26, 28 for securing probe 10 to the skin. Outer tape 12 is preferably made from an opaque microfoam material, for example, Stock No. 977L, manufactured by the 3M Company of St. Paul, Minn.

Referring to FIGS. 2 and 4, light block tape 14, preferably adhesive-coated on both sides, may be made from a material known in the industry as Kodak Optical Flat Black. In the illustrated embodiment, light block 14 comprises a pair of flat, preferably square end portions 15 spanned by a narrow central connecting portion 17. In an alternative embodiment, portion 17 is omitted, and opposed, flat plates 15 comprise separate pieces. At least one side of light block tape 14 bears a black light block layer (e.g., Coating Sciences # S121). Light block tape 14, of smaller dimensions than outer tape 12, overlies a portion of lower inner surface 34 of outer tape 12 and isolates the transilluminated tissue from extraneous light sources (e.g., room lighting, sunlight, etc.), thereby improving the signal-to-noise ratio of probe 10.

Sensor assembly 16, shown in FIG. 5, includes a miniature light-emitting diode (LED) 36, a miniature photoreceptor (photosensor) 38, and lead wires 40 connecting the LED 36 and photosensor 38 to a cable 42. A 9-pin plug connector 44, attached to the other end of the cable 42, is configured to interface with a conventional oximeter box (not shown). Sensor assembly 16 is adhesively secured to light block tape 14 with LED 36 and photosensor 38 disposed at the center of each of square end portions 15 (see FIG. 10) and wires 40 extending along connecting portion 17.

Inner tape 20, preferably adhesive coated on both sides, secures assembly 16 and alignment member 18 to outer tape 12. Inner tape 20 includes respective spaced windows 46 of transparent plastic (FIG. 7) positioned over and in registration with each of LED 36 and photosensor 38. Inner tape 20 is preferably opaque other than at windows 46, and may comprise one tape as shown or three pieces of tape overlying one another, e.g., one at each ends and a central tape having windows 46 overlying the ends of the other two.

U-shaped alignment member 18 is disposed between light block tape 14 and inner tape 20 to maintain the overall configuration of the device, and particularly to maintain alignment between the LED and photosensor. In the illustrated embodiment, member 18 is a thin, resilient, flat, elongated (generally rectangular) piece of plastic having a central slot or gap 19 which extends more than half the length of member 18. LED 36 and photosensor 38 are positioned within slot 19 near opposite ends thereof. Parallel rod portions 21 of member 18 on either side of slot 19 preform probe 10 into a U-shaped configuration which renders probe 10 easier to mount on a human extremity, partioularly a finger. Rods 21 each have curved, preferably semicircular bight portions 21A (FIG. 6A) so that straight, upper and lower leg portions 21B thereof are generally parallel to each other (see FIG. 6A). In an alternative embodiment shown in FIG. 6B, an alignment member 18A is fashioned in a bent U-shape with only one curved end connecting portion 23, rather than two end portions as shown in FIG. 2.

Alignment member 18 or 18A is preferably made from a lightweight, shape-retentive polypropylene such as FINA 3622 manufactured by the Fina Oil and Chemical Company of Dallas, Tex. Alignment member 18 or 18A is preferably highly resilient, i.e., sufficiently resilient so that alignment member 18 can assume a substantially planar configuration without breaking during assembly of probe 10. When the fully assembled probe 10 is removed from the assembly tooling, alignment member 18 or 18A instantly snaps back to its overall U-shaped configuration. By means of the shape memory of member 18 or 18A, probe 10 assumes a corresponding U-shaped configuration when undeformed, as shown in FIG. 1B.

Conventional flexible, planar sensors suffer the inherent problem of requiring precise manual alignment of the LED opposite the photosensor so that the maximum amount of light emitted by the LED is received by the photosensor. Inasmuch as the undersurface of existing sensors is typically coated with a pressure sensitive adhesive, the sensor has a tendency to adhere to the patient before a physician or technician can establish the optimum alignment between the LED and photosensor. Moreover, it is cumbersome to remove the sensor and re-apply it to the patient to compensate for misalignment between the LED and photosensor. The problem is exacerbated in many critical care applications, for example, during emergency surgery, when health care professionals often lack the time to ensure proper alignment between the LED and photosensor. As a result, sometimes only a small fraction of the light emitted by the LED is received by the photosensor.

In the probe of the invention these problems are addressed not only by the overall U-shaped configuration of probe 10 provided by alignment member 18, but also by the provision of positioning slide 22 which further facilitates proper alignment of the LED and photosensor. As shown in FIGS. 1A, 2 and 8, positioning slide 22 comprises a rectangular piece of a smooth-surfaced plastic tape free of adhesive on its outer surface. Slide 22 is disposed on adhesive-coated lower inner surface 34 of outer tape 12 covering cable 42. In this way, the inner rectangular region of lower surface 34 defined by the positioning slide 22 remains adhesive-free, thus permitting the patient's finger to move freely along the positioning slide 22 until the finger abuts the bottom U-shaped end of probe 10. This reduces the risk that the sensor will stick to the patient before the LED 36 and photosensor 38 can be properly aligned.

Referring now to FIGS. 1B, 2, 9, and 10, release tape assembly 24 includes release tapes 50 and 52 configured to releasably adhere to the inside surface of probe 10. More particularly, release tape 50 overlies bottom wings 26 of outer tape 12, concealing positioning slide 22 and portions of inner tape 20, electrical assembly 16, alignment member 18, and light block 14. Tape 52 comprises an enlarged end portion 54 and a pull tab 56. End portion 54 overlies top wings 28 of outer tape 12 and conceals the remaining portion of the inside surface of the probe. Pull tab 56 extends freely over release tape 50. Release tape assembly 24 thus protects the adhesive surfaces of probe 10 until it is ready for use.

To apply probe 10 to a patient, the user first pulls upon the end 55 of pull tab 56 to remove release tape 52 and fully expose release tape 50. Release tape 50 is then removed by pulling up its outer edge 58, exposing lower inner surface 34 of outer tape 12 and the various subcomponents, all of which are adhesive-coated except for the central, adhesive-free area defined by positioning slide 22 on lower inner surface 34. The patient's finger is then guided along positioning slide 22, passing through an imaginary line between LED 36 and photosensor 38, until the finger abuts the closed, U-shaped, inner end 60 of probe 10. When probe 10 is applied to a patient in the foregoing manner, alignment member 18 ensures proper alignment of the patient's finger, LED 36, and photosensor 38 without the need for the user to manually align the LED and photosensor.

Certain features of probe 10 according to the invention, particularly size and precise configuration, are dictated by the intended end use. Oximeter probes according to the present invention are preferably made in sizes for adult, pediatric, infant and neonatal use.

It will be understood that the foregoing description is of preferred exemplary embodiments of the invention, and that the invention is not limited to the specific forms shown. For example, a variety of thin, flexible materials could be substituted for the particular tapes and plastics described, and means other than adhesives, such as hook-and-loop closures or other fasteners, could be used to secure the probe to the patient. These and other modifications may be made in the design and arrangement of the elements without departing from the scope of the invention as expressed in the appended claims.

We claim:

1. A noninvasive, electrooptical sensor probe for removable attachment to the skin of a patient to measure light extinction during transillumination of the blood-perfused tissue beneath the skin, comprising:
    a flexible, substantially U-shaped, support structure having spaced, opposed upper and lower inner surfaces;
    a light source mounted in said support structure and positioned to emit light from one of said inner surfaces;
    a photosensor mounted in said support structure and positioned on the other of said inner surfaces to detect light emitted by said light source;
    means for electrically connecting said light source and said photosensor to an external device;
    means for removably securing said support structure to the skin; and
    a generally U-shaped, highly resilient alignment mementer disposed in said support structure to impart a U-shape thereto, which alignment member extends substantially from said light source to said photosensor.

2. The probe of claim 1, wherein said alignment member is made of a highly resilient plastic.

3. The probe of claim 1, wherein said securing means comprises an adhesive.

4. The probe of claim 1, wherein the light source comprises a light-emitting diode.

5. The probe of claim 1, further comprising a smooth, non-adhesive slide centrally disposed on said lower inner surface of said support structure and configured to facilitate insertion of a finger along said slide to an inner end of said probe.

6. A noninvasive, electrooptical sensor probe for removable attachment to the skin of a patient to measure light extinction during transillumination of the blood-perfused tissue beneath the skin, comprising:
    a flexible, substantially U-shaped support structure having spaced, opposed upper and lower inner surfaces;
    a light source mounted in said support structure and positioned to emit light from one of said inner surfaces;
    a photosensor mounted in said support structure and positioned on the other of said inner surfaces to detect light emitted by said light source;
    means for electrically connecting said light source and said photosensor to an external device;
    means for removably securing said support structure to the skin; and
    a generally U-shaped alignment member disposed in said support structure to impart a U-shape thereto, which alignment member extends substantially from said light source to said photosensor;
    wherein said alignment member comprises a pair of parallel, U-shaped rods which extend in the lengthwise direction of said support structure on opposite sides of said light source and said photosensor.

7. The probe of claim 6, wherein said alignment member has at least one end portion uniting said U-shaped rods.

8. A noninvasive, electrooptical sensor probe for removable attachment to the skin of a patient to measure light extinction during transillumination of the blood-perfused tissue beneath the skin, comprising:
    a flexible, substantially U-shaped support structure having spaced, opposed upper and lower inner surfaces;
    a light source mounted in said support structure and positioned to emit light from one of said inner surfaces;
    a photosensor mounted in said support structure and positioned on the other of said inner surfaces to detect light emitted by said light source;
    means for electrically connecting said light source and said photosensor to an external device;
    means for removably securing said support structure to the skin;

a generally U-shaped, alignment member disposed in said support structure to impart a U-shape thereto, which alignment member extends substantially from said light source to said photosensor; and a smooth, non-adhesive slide centrally disposed on said lower inner surface of said support structure and configured to facilitate insertion of a finger along said slide to an inner end of said probe;

wherein said electrical connecting means comprises a cable terminating in a plug connector at an end thereof remote from said support structure, and said slide comprises a piece of tape which covers a portion of said cable that extends lengthwise into said support structure.

* * * * *

UNITED STATES PATENT AND TRADEMARK OFFICE
CERTIFICATE OF CORRECTION

PATENT NO. : 5,217,012

DATED : June 8, 1993

INVENTOR(S) : Robert L. Young, et al.

It is certified that error appears in the above-identified patent and that said Letters Patent is hereby corrected as shown below:

Claim 1, col. 6, lines 8-9, change "mementer" to --member--.

Signed and Sealed this

Fourth Day of October, 1994

Attest:

BRUCE LEHMAN

Attesting Officer

Commissioner of Patents and Trademarks